1

(12) United States Patent
Stanjek et al.

(10) Patent No.: US 8,933,259 B2
(45) Date of Patent: Jan. 13, 2015

(54) CONTINUOUS PROCESS FOR PREPARING SIOC-CONTAINING COMPOUNDS

(75) Inventors: Volker Stanjek, Ampfing (DE); Nicolas Imlinger, St. Pantaleon (AT); Heribert Westermayer, Burghausen (DE); Wolfgang Wewers, Burghausen (DE)

(73) Assignee: Wacker Chemie AG, Munich (DE)

( * ) Notice: Subject to any disclaimer, the term of this patent is extended or adjusted under 35 U.S.C. 154(b) by 0 days.

(21) Appl. No.: 14/005,121

(22) PCT Filed: Mar. 9, 2012

(86) PCT No.: PCT/EP2012/054108
§ 371 (c)(1),
(2), (4) Date: Sep. 13, 2013

(87) PCT Pub. No.: WO2012/123356
PCT Pub. Date: Sep. 20, 2012

(65) Prior Publication Data
US 2014/0005433 A1    Jan. 2, 2014

(30) Foreign Application Priority Data
Mar. 15, 2011  (DE) .................. 10 2011 005 581

(51) Int. Cl.
*C07F 7/18*  (2006.01)

(52) U.S. Cl.
CPC ..................................... *C07F 7/188* (2013.01)
USPC ........................... 556/457; 556/467; 556/471

(58) Field of Classification Search
CPC ....... C07F 7/0896; C07F 7/1876; B01D 3/14; F28D 2021/0064
USPC ..................... 556/425, 467, 471, 457; 203/89
See application file for complete search history.

(56) References Cited

U.S. PATENT DOCUMENTS

| 2,520,391 | A | * | 8/1950 | Findlay ......................... 208/317 |
| 4,366,324 | A | * | 12/1982 | Habata et al. ................. 556/460 |
| 4,924,022 | A |   | 5/1990 | Bank et al. |
| 5,423,952 | A | * | 6/1995 | Stout ............................. 202/174 |
| 5,779,993 | A |   | 7/1998 | Gentry |
| 6,177,584 | B1 |   | 1/2001 | Loewenberg et al. |
| 6,242,628 | B1 |   | 6/2001 | Kropfgans et al. |
| 2002/0086907 | A1 |  | 7/2002 | Standke et al. |
| 2006/0167297 | A1 |  | 7/2006 | Schattenmann et al. |

FOREIGN PATENT DOCUMENTS

| EP | 0997468 A2 | 5/2000 |
| EP | 0999215 A2 | 5/2000 |
| EP | 1205505 A2 | 5/2002 |
| EP | 1686132 A1 | 8/2006 |
| JP | 2002045602 A | 2/2002 |

OTHER PUBLICATIONS

Organikum, Deutscher Verlag der Wissenschaften, Berlin 1976, ISBN 3-326-00076-6; chapter 2.3.3.1., pp. 58-63, No translation is provided. However, relevance is provided.

* cited by examiner

*Primary Examiner* — Sudhakar Katakam
*Assistant Examiner* — Pancham Bakshi
(74) *Attorney, Agent, or Firm* — Brooks Kushman P.C.

(57) ABSTRACT

Organosilicon compounds bearing SiOC groups and having low residual silicon-bonded chlorine are prepared continuously by reacting a chlorosilane with alcohol and optionally water by contacting a gaseous phase containing alcohol with a liquid phase containing silane, organosilicon intermediates, organosilicon compounds containing SiOC groups and optional inert solvent in a reaction column in which the gas phase passes through the liquid phase in bubble form, or is provided with a vaporizer operating by a crossflow principle.

18 Claims, 3 Drawing Sheets

CONTINUOUS PROCESS FOR PREPARING SIOC-CONTAINING COMPOUNDS

CROSS-REFERENCE TO RELATED APPLICATIONS

This application is the U.S. National Phase of PCT Appln. No. PCT/EP2012/054108 filed Mar. 9, 2012, which claims priority to German application DE 10 2011 005 581.9 filed Mar. 15, 2011, the disclosures of which are incorporated in their entirety by reference herein.

BACKGROUND OF THE INVENTION

1. Field of the Invention

The invention relates to a continuous process for preparing SiOC-containing compounds, preferably for preparing alkoxysilanes and alkoxy-rich silicone resins.

2. Description of the Related Art

This process, which is usually referred to as "alkoxylation", proceeds from the corresponding chlorosilanes, the silicon-bonded chlorine atoms of which are exchanged for alkoxy groups. This is possible through a reaction of the chlorosilanes with the particular alcohol or else an alcohol-water mixture with release of hydrochloric acid. If the pure alcohol is used, this gives alkoxysilanes, whereas the use of alcohol-water mixtures leads to the formation of alkoxy-functional siloxanes. In this case, the mean molecular mass of the siloxanes formed can be varied virtually as desired via the water content of the alcohol-water mixtures used.

For reasons of cost, it is desirable to perform the alkoxylation in a continuous operation. Corresponding processes are already known and are described, for example, in EP 1205505 or EP 1686132, and the references cited therein.

These alkoxylation processes are typically performed in plants consisting of a (pre)reactor and one or two columns for a reactive distillation. FIG. 1 shows a schematic diagram of the plant for the continuous alkoxylation process described in EP 1686132. Column 2 which is shown in FIG. 1 is optional in principle, but the use of the second column is advantageous for attainment of a product quality containing only a small proportion of silicon-bonded chlorine atoms.

In such a plant, alcohol and chlorosilane are contacted with one another countercurrently. Thus, the chlorosilane is first contacted in an upstream reactor with a usually substoichiometric amount of alcohol based on the chlorine atoms, forming a partly alkoxylated silane product and gaseous hydrogen chloride. The alcohol can be added directly or else can originate (in a form with a higher or lower hydrochloric acid content) from column 1 or else column 2. The hydrogen chloride is removed as an offgas from the plant, whereas the silane is transferred into the column 1 and fed into the upper column part thereof or even at the top of the column.

In column 1, the silane flows from the top downward, whereas the particular alcohol is vaporized by means of a circulation vaporizer at the foot of the column and is moved in the opposing direction in gaseous form. The column 1 offers a large surface area between gaseous and liquid phases through insertions of random packing, and so there is intense contact between silane and alcohol. It is thus possible to exchange the silicon-bonded chlorine atoms still present for alkoxy groups. The silane having a distinctly lower chlorine level is finally removed from the distillation pot of the circulation vaporizer, whereas the alcohol, which is accordingly in hydrochloric acid solution, is obtained at the top of column 1.

The acidic alcohol can be passed on into the reactor, whereas the silane, according to the purity, can be utilized directly as the end product or else transferred into column 2.

Column 2 works by an identical principle to column 1 and serves—if necessary—for further depletion of silicon-bonded chlorine atoms in the silane phase. The alcohol-hydrochloric acid mixture obtained via the top can be passed on into column 1 or else alternatively directly into the reactor.

In this case, it is possible to use the entire amount of alcohol required for the operation at the foot of column 2 and to conduct it counter to the silane stream through both reaction columns. However, it is likewise also possible to add a portion of the process alcohol at other points, for example at the foot or else various metering points in column 1, or not until within the reactor.

It will be appreciated that it is likewise possible to conduct this operation not with the pure alcohol but instead with an alcohol-water mixture. In this case, the water substitutes as many as two chlorine atoms on different silicon atoms, such that a siloxane unit is the ultimate result. Instead of monomeric alkoxysilanes, oligomeric siloxanes rich in alkoxy groups are thus obtained. However, this does not change anything about the principle of operation detailed above.

In this continuous operation, it is desirable to attain maximum conversion, or as already stated, to obtain a product containing only a minimum number of silicon-bonded chlorine atoms, if any. Thus, chlorine atoms remaining on the silicon atom would be easily substitutable by other compounds having active hydrogen, and there would therefore be a release of chloride or hydrochloric acid in downstream synthesis stages and/or applications of the particular products, and this would almost always have a massively disruptive effect. There are known processes for reprocessing of alkoxysilanes and/or alkoxysiloxanes having chloride radicals remaining on the silicon, for example from EP 0999215 or EP 0997468, but any reprocessing operations are associated with additional operating steps. For reasons of cost, it is therefore always advantageous when the alkoxylation operation leads directly to alkoxysilanes and/or alkoxysiloxanes with a sufficiently low content of silicon-bonded chlorine atoms.

As well as very substantially complete removal of the silicon-bonded chlorine, it is of course likewise desirable to use the alcohol required for this purpose or the alcohol-water mixture required for this purpose only in a slightly superstoichiometric amount, if at all, and accordingly to obtain very substantially pure hydrogen chloride as the coproduct. This is all the more true in that the alcohol used in excess is of course obtained not in pure form but as a mixture with hydrogen chloride. In this acidic alcohol, there is nucleophilic substitution of the alcoholic hydroxyl group by the chloride even at room temperature. In other words, the corresponding chloroalkanes and water are formed. Workup of these complex mixtures of alcohol, chloroalkane, water and hydrogen chloride with the aim of obtaining reusable materials of value is usually very complex and not very cost-effective.

The aim of arriving at sufficiently low-chlorine alkoxysilanes without any great alcohol excesses, however, is achieved in the processes according to the prior art only for a few selected silanes. Especially silanes having relatively large silicon-bonded alkyl groups can be alkoxylated only extremely incompletely by these processes and/or require great alcohol excesses.

The problem addressed was therefore that of developing a process for alkoxylating chlorosilanes, which has these disadvantages of the processes according to the prior art only to a distinctly reduced degree, if at all.

SUMMARY OF THE INVENTION

The invention provides a process for continuously preparing compounds (SC) containing SiOC groups, in which a silane (SI) having silicon-bonded chlorine atoms is reacted with an alcohol (A) and optionally water to release hydrogen chloride, at least part of the reaction being performed in a reaction column in which the gaseous phase (PG) contains a total of at least 80% by weight of alcohol (A), hydrogen chloride and any water and any inert gas, and the liquid phase (PF) contains a total of at least 80% by weight of silane (SI), silicon-containing intermediates (SB) and compounds (SC) containing SiOC groups and any inert solvent, characterized in that the alcohol (A) is passed repeatedly through the liquid phase (PF)
a) by virtue of the reaction column being provided with internals (E) which pass the gas phase (PG) through the liquid phase (PF) in bubble form and/or
b) by virtue of the reaction column being provided with a vaporizer (V) which works by a crossflow principle.

DETAILED DESCRIPTION OF THE PREFERRED EMBODIMENTS

Figure 1:
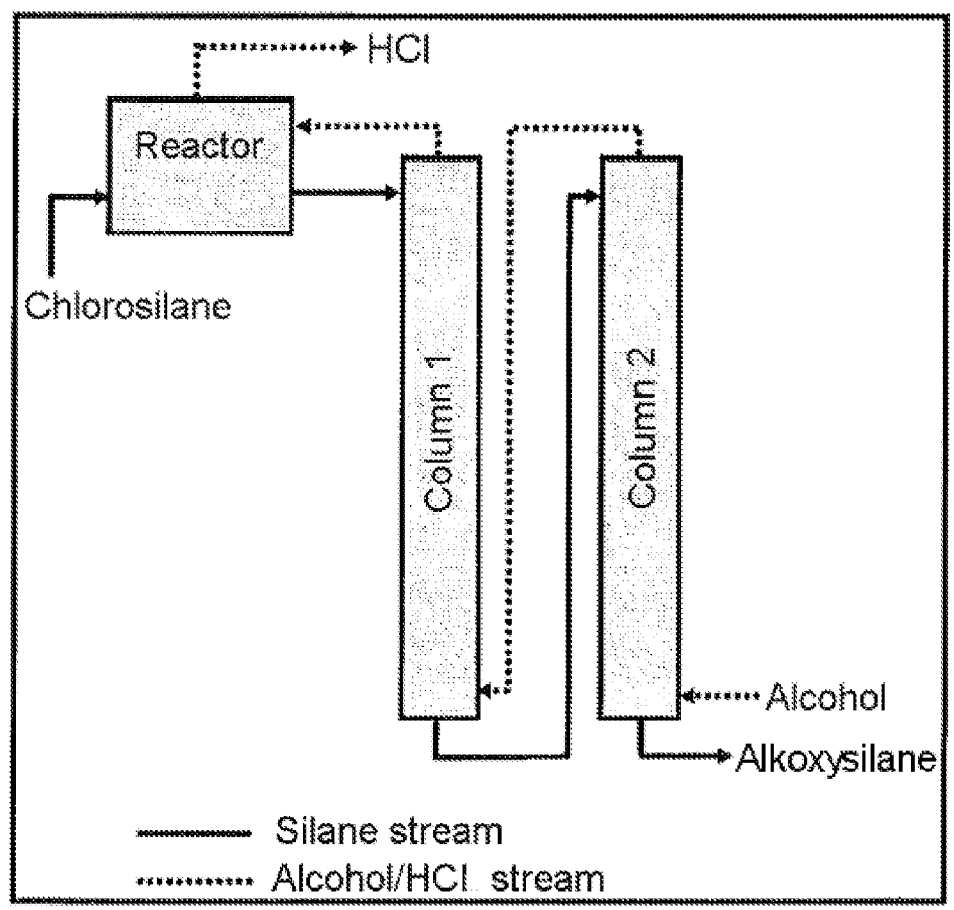
FIG. 1 illustrates a prior art continuous process in accordance with EP 1686132.

All constituents both of the liquid phase (PF) and of the gas phase (PG) add up to 100% by weight in each case.

The vaporizer (V) which works by a crossflow principle has the characteristic that the liquid silicon-containing compounds (SI), (SB) and/or (SC) coming from the column flow along a path which has at least 2 metering points for the alcohol (A) to be vaporized and the alcohol (A) is at least partly vaporized between these metering points, the vaporized alcohol (A) in the individual segments being combined and transferred at least in parts into the column. In the course of this, the gas stream in one segment does not go through the liquid phase of the prior segment. The silicon-containing compounds (SI), (SB) and/or (SC) are obtained in liquid form at the end of the path. In other words, the stream of the alcohol to be vaporized in the vaporizer (V) does not run counter to the stream of the silicon-containing compounds coming from the column but "crosses" it.

Preferably, the gaseous phase (PG) present in the column contains a total of at least 90% by weight and more preferably at least 95% by weight of alcohol, hydrogen chloride and any water and any inert gas.

The inert gas used may, for example, be nitrogen, air, noble gases or vaporized solvents, preferably volatile solvents such as ethers (e.g. diethyl ether, THF), esters (e.g. ethyl acetate), hydrocarbons (e.g. methane, ethane, propane, butane), ketones (e.g. acetone). However, preference is given to dispensing with the use of an inert gas.

The liquid phase (PF) present in the reaction column preferably contains a total of at least 90% by weight and more preferably at least 95% by weight of silane (SI), silicon-containing intermediates (SB) and compounds (SC) containing SiOC groups, and any inert solvents.

Inert solvents are preferably aprotic solvents or solvent mixtures. Examples of such solvents are ethers, such as dioxane, tetrahydrofuran, diethyl ether, diisopropyl ether, diethylene glycol dimethyl ether; chlorinated hydrocarbons, such as dichloromethane, trichloromethane, tetrachloromethane, 1,2-dichloroethane, trichloroethylene; hydrocarbons, such as pentane, n-hexane, hexane isomer mixtures, heptane, octane, white spirit, petroleum ether, benzene, toluene, xylenes; siloxanes, especially linear dimethylpolysiloxanes having trimethylsilyl end groups having preferably 0 to 6 dimethylsiloxane units, or cyclic dimethylpolysiloxanes having preferably 4 to 7 dimethylsiloxane units, for example hexamethyldisiloxane, octamethyltrisiloxane, octamethylcyclotetrasiloxane and decamethylcyclopentasiloxane; ketones, such as acetone, methyl ethyl ketone, diisopropyl ketone, methyl isobutyl ketone (MIBK); esters, such as ethyl acetate, butyl acetate, propyl propionate, ethyl butyrate, ethyl isobutyrate; carbon disulfide and nitrobenzene, or mixtures of these solvents.

Nonvolatile solvents are preferred, for example sulfolane, N-methylpyrrolidone, DMSO and DMF.

However, preference is given to dispensing with the addition of an inert solvent. The liquid phase (PF) contains preferably at least 80% by weight, more preferably at least 90% by weight and most preferably at least 95% by weight of silane (SI), silicon-containing intermediates (SB) and compounds (SC) containing SiOC groups.

The hydrogen chloride formed in the alkoxylation and any as yet unreacted amounts of alcohol are preferably drawn off at the top of the reaction column. The compounds (SC) which contain SiOC groups and are formed in the alkoxylation are preferably obtained from the vaporizer (V).

The invention is based on the surprising fact that the intense contact, between the liquid phase (PF) comprising the silicon-containing compounds and the alcohol (A), which is forced in accordance with the invention, leads to a product (SC) with a distinctly lower residual content of silicon-bonded chlorine atoms. This is extremely remarkable in that it was to be assumed according to the prior art that a conventional column with random packing and having a conventional vaporizer, for example a circulation vaporizer, also leads to sufficiently intense contact between the two abovementioned streams. However, this is surprisingly not the case.

Figure 2:
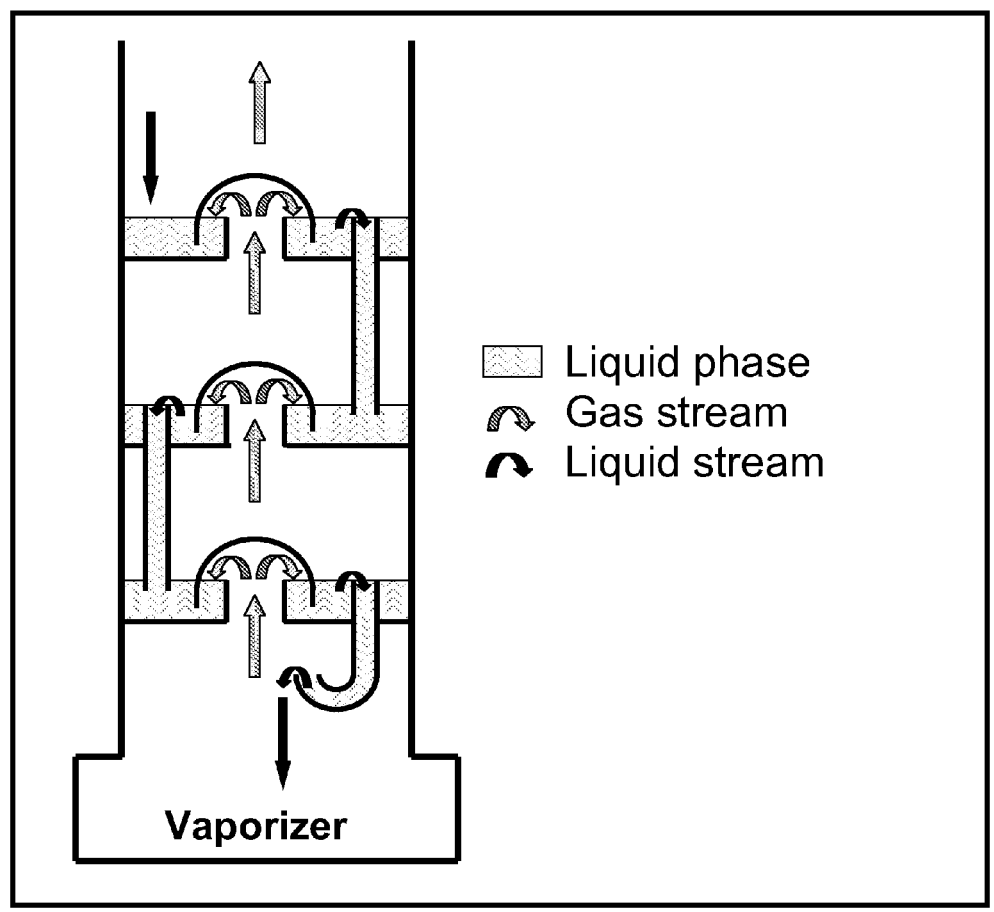
FIG. 2 illustrates one embodiment of the invention.

Preferably, the abovementioned column internals (E), which pass the gas stream (PG) through the liquid phase (PF) in bubble form, are bubble-cap trays. The principle of bubble-cap tray columns has long been known and is described in numerous textbooks, for example in Organikum, Deutscher Verlag der Wissenschaften, Berlin 1976, ISBN 3-326-00076-6. In addition, the way in which a bubble-cap tray column works is shown schematically in FIG. 2: while the liquid phase (PF) stands on each tray and flows gradually downward from tray to tray through overflows, the gas stream (PG) flows upward through what are called bubble caps, being conducted through the liquid phase (PF) in bubble form as it passes through each bubble cap. Preferably, a typical bubble-cap tray has not just one bubble cap but numerous bubble caps, at least 2 and especially at least 5 individual bubble caps. The internals (E) preferably have at least 2, more preferably at least 3 and especially at least 5 bubble-cap trays.

Such bubble-cap tray columns have never been used to date for continuous alkoxylations, and it is completely surprising that they lead to much better results than the columns with random packing which are established in this operation and are typically used, as described in the prior art (EP 1686132 inter alia).

A preferred embodiment of a vaporizer (V) working by the crossflow principle has at least two and especially at least 4 segments through which the liquid phase (PF) coming from the reaction column has to flow successively, with metered addition and vaporization of alcohol (A) in each of these segments, and the gaseous alcohol stream (PG) which forms in the individual segments is combined and at least partly transferred into the reaction column. In the course of this, the gas stream (PG) of any segment does not go through the liquid phase (PF) of the prior segment. The liquid products (SC) containing SiOC groups are discharged from the last segment.

The vaporizer (V) used is preferably a poolboiler or kettle type, the shell space of which is divided by upright baffle plates into individual segments, specifically into at least 3 and more preferably at least 4 segments. The liquid phase (PF) coming from the reaction column has to flow through these segments according to the principle of weir overflow at the baffle plates, with addition and vaporization of alcohol (A) in each of these segments, and the gaseous alcohol stream (PG) which forms in the individual segments is combined and at least partly transferred into the reaction column. This vaporization principle is referred to hereinafter as a segment vaporizer (V).

Figure 3:
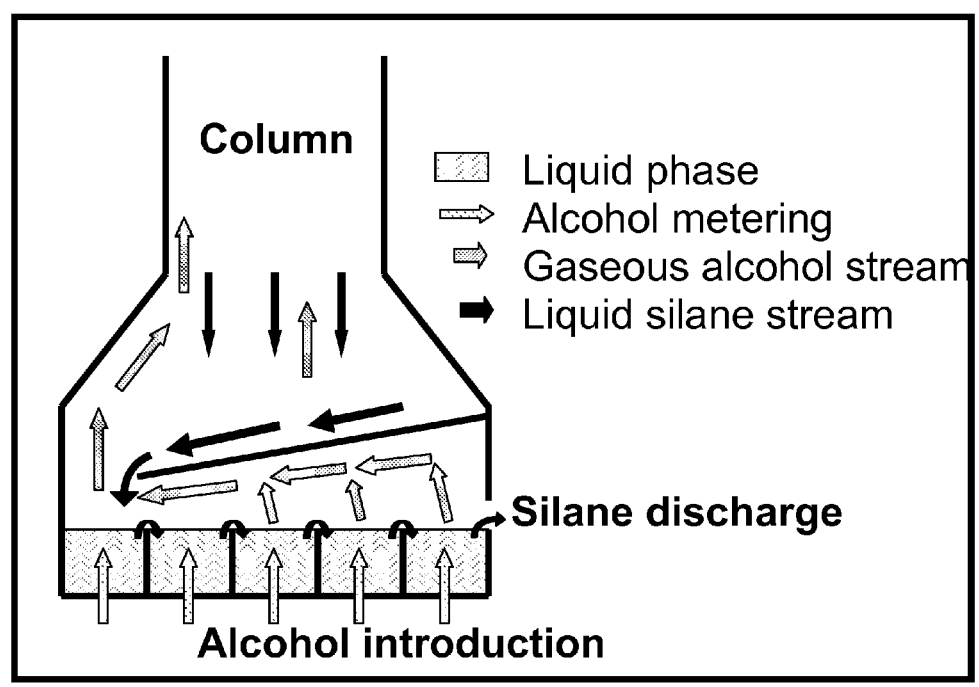
FIG. 3 illustrates a further embodiment of the invention.

The way in which a typical segment vaporizer (V) works is shown schematically in FIG. 3: the liquid phase (PF) coming from the reaction column is transferred into a first segment. It flows from there successively into further segments until it is ultimately discharged from the last segment. In each of these segments, alcohol (A) is introduced and vaporized. The vaporized alcohol (PG) in the individual segments is combined and preferably transferred into the reaction column. In the course of this, the gas stream of any segment (PG) does not go through the liquid phase (PF) of the prior segment. The amount of alcohol (A) introduced into the various segments may be the same or different.

Optionally, the residual chloride content can be reduced further in the last segment chamber by adding not only the alcohol (A) but also a metal alkoxide, preferably an alkali metal alkoxide of the corresponding alcohol.

A further preferred embodiment of a vaporizer (V) which works by the crossflow principle consists of a falling-film or thin-film evaporator, in which the liquid phase (PF) coming from the reaction column is metered in the upper falling-film/thin-film apparatus region and then runs along the wall of the falling-film or thin-film evaporator, with metered addition of the alcohol (A) to be vaporized at at least two points within the falling-film or thin-film apparatus. It is metered in preferably at at least three and more preferably at at least four different points. The alcohol (A) can either be metered in through orifices in the wall of the falling-film or thin-film evaporator or by spraying the alcohol (A) from metering points within the evaporator against the evaporator wall.

The alcohol (A) added is vaporized at least in portions in the thin-film or falling-film evaporator, and the gaseous alcohol stream (PG) which forms is at least partly transferred into the column. The products (SC) containing SiOC groups are discharged from the evaporator in liquid form at an outlet at the end of the thin-film or falling-film zone.

Typically—irrespective of the specific embodiment of the vaporizer (V)—at least 60% of the alcohol (PG) vaporized in the vaporizer (V) is transferred into the reaction column, preferably at least 80% of the vaporized alcohol (PG) being transferred into the column, and more preferably all of the vaporized alcohol (PG) being transferred into the column.

Typically, the liquid compounds (SC) containing SiOC groups which are discharged from the inventive vaporizer (V) have an alcohol content of <8%, preferably <3% and more preferably <1%.

In order to achieve the desired low alcohol concentrations in the compounds (SC) discharged from the vaporizer (V), it is advantageous when the vaporization temperature at the end of the vaporization zone is higher than at the start thereof. If the vaporizer (V) is a segment vaporizer, this can be achieved by virtue of the temperature in the last segment of the vaporizer (V) being higher than in all or at least some prior segments. It is particularly favorable when the temperature of the liquid phase (PF) rises from segment to segment according to the flow direction.

If the vaporizer (V) is one of the above-described falling-film or thin-film evaporators, the desired profile of the vaporization temperature can be achieved by corresponding regulation of the vaporizer output.

In a preferred embodiment of the process according to the invention, some of the inventive reaction is performed in a prereactor. The prereactor may comprise, for example, a stirred tank, a tubular reactor or a loop reactor with or without forced circulation. In this prereactor, the silane (SI) which serves as the reactant reacts with alcohol (A) or an alcohol-water mixture. The hydrogen chloride formed is removed in gaseous form from the reaction mixture, and the product mixture formed, which still comprises significant amounts of silicon-bonded chlorine atoms, is transferred into a first reaction column.

If the process according to the invention is performed only with one reaction column, this first reaction column is a column with internals (E) and/or a vaporizer (V).

Preferably, an optionally water-containing alcohol-hydrochloric acid mixture is used in the prereactor, this originating from the first reaction column or—if present—from the second or a further reaction column.

In a further preferred version of the process according to the invention, the inventive reaction is performed at least partly in two or more reaction columns. In this case, all reaction columns or else only one or some of the reaction columns may be provided with internals (E) and/or a vaporizer (V). In the latter case, the last reaction column in terms of flow direction of the liquid phase (PF) has preferably been provided with internals (E) and/or a vaporizer (V).

More preferably, the process according to the invention is performed in a plant consisting of a prereactor and two or more reaction columns. In this case, all reaction columns, or else only one or some of the reaction columns, may be provided with internals (E) and/or a vaporizer (V). In the latter case, the last reaction column in terms of flow direction of the liquid phase (PF) has preferably been provided with internals (E) and/or a vaporizer (V).

The silanes (SI) which serve as the reactant are preferably first partially reacted in the prereactor with the alcohol (A) or an alcohol-water mixture. Thereafter, the liquid phase (PF) is successively passed through the individual reaction columns in which the inventive conversion is continued. Preferably, the liquid phase (PF) is in each case metered in close to the top of the column and removed from the reaction column at the foot of the column or from the vaporizer (V) of the respective reaction column. A typical path of the liquid phase (PF) through such a plant consisting of a prereactor and at least two reaction columns is shown schematically in FIG. 1. At the foot or from the vaporizer (V) of the last reaction column, the product (SC) containing SiOC groups having the already above-described alcohol content of <8%, preferably <3% and more preferably <1% is obtained.

The aqueous or nonaqueous alcohol, the alcohol-hydrochloric acid mixture which forms during the reaction and the substantially pure hydrogen chloride which ultimately forms in the case of complete consumption of the alcohol (A) or alcohol-water mixture used can also be conducted through the plant as outlined in FIG. 1. However, it may be more favorable not to add all of the alcohol (A) or all of the alcohol-water mixture already at the foot or in the vaporizer of the column 2. For instance, a portion of the alcohol (A) or of the alcohol-water mixture may also only be introduced into the process at another point.

It is particularly favorable when a portion of the alcohol (A) is added at the foot of or in the vaporizer of column 2, and the alcohol-hydrochloric acid mixture obtained at the top of this column is transferred in condensed or gaseous form directly into the prereactor. The rest of the process alcohol is added at least in large portions at the foot of column 1. This variant of the process according to the invention has the advantage that the hydrogen chloride released in column 2 is no longer passed through column 1.

If the inventive operation is performed in a plant consisting of a prereactor and at least 2 reaction columns and—this constituting a preferred embodiment of the invention—only the last reaction column in each case in terms of the flow direction of the liquid phase (PF) has been provided with the internals (E) and/or the vaporizer (V), it may be the case that only a relatively low portion of the overall reaction takes place in this reaction column. In spite of this, this reaction column with the internals (E) and/or the vaporizer (V) is advantageous in order to obtain a product (SC) with a minimum content of silicon-bonded chlorine atoms.

Preferably, in the column with the internals (E) and/or the vaporizer (V), the content in liquid phase (PF) of silicon-bonded chlorine atoms is reduced by 50%, more preferably by at least 70% or even by at least 90%.

Preferably, the temperature in the reaction columns, especially in the reaction column(s) having internals (E) and/or a vaporizer (V), is at least 20° C., more preferably at least 40° C., especially at least 60° C., and at most 160° C., more preferably at most 140° C., especially at most 130° C.

The gaseous hydrogen chloride which forms as a by-product in the process is preferably freed of higher-boiling impurities, which can in turn be recycled back into the process. The gaseous hydrogen chloride can then be used further as a material of value.

Preferably, the process according to the invention serves for preparation of monomeric alkoxysilanes, i.e. in the process according to the invention preference is given to using alcohols (A) having a water content of <8%, preferably <4% and more preferably <2%.

Preferably, in the process according to the invention silanes (SI) of the general formula (1) are used $$R_nSiCl_{4-n} \quad (1)$$

where
n is 0, 1, 2 or 3, and
R is hydrogen or a monovalent substituted or unsubstituted organic radical.

If a plurality of R radicals are present, these may be the same or different.

Examples of R are hydrogen and hydrocarbyl radicals such as methyl, ethyl, vinyl, n-propyl, i-propyl, allyl, n-butyl, i-butyl, t-butyl, n-pentyl, i-pentyl, t-pentyl, cyclopentyl, n-hexyl, i-hexyl, t-hexyl, cyclohexyl, n-heptyl, i-heptyl, t-heptyl, n-octyl, i-octyl, and the various regioisomers of nonyl, decyl, undecyl, dodecyl, tridecyl, tetradecyl, pentadecyl, hexadecyl, heptadecyl, octadecyl etc. Further examples are aromatic R radicals such as phenyl or tolyl. It is also possible for the R radicals to be substituted, for example by halogens, as, for example, in the case of the chloromethyl or chloropropyl radical. The hydrocarbyl radicals R preferably have at least 1 and at most 28, especially at most 18, carbon atoms. Preference is given to alkyl radicals R. Further examples of R are γ-acryloyloxypropyl, γ-methacryloyloxypropyl, acryloyloxymethyl or methacryloyloxymethyl radicals.

Preferably, the process according to the invention is employed for alkoxylation of the comparatively nonvolatile silanes (SI) of the general formula (1) containing at least 6 carbon atoms, preferably at least 7 and more preferably at least 10 carbon atoms in one or more R radicals.

Thus, it has been found that, surprisingly, alkoxylation of such comparatively nonvolatile silanes (SI) having correspondingly large silicon-bonded alkyl radicals by the processes according to the prior art is particularly poor. In other words, residual contents of silicon-bonded chlorine atoms below 50 ppm by weight are usually unachievable, or at best achievable using very large alcohol excesses, in the case of these silanes (SI) with these processes without aftertreatment of the respective products. Likewise surprising was the discovery that the results of the continuous alkoxylation can be distinctly improved by use of the process according to the invention in the case of these silanes (SI).

Examples of silanes (SI) of the general formula (1), which are preferably alkoxylated using the process according to the invention, are n-octyl- or i-octyltrichlorosilane.

Particular preference is given to using the process according to the invention for alkoxylation of the comparatively nonvolatile silanes (SI) of the general formula (1) which have an R radical having at least 10 carbon atoms, which have at least 2 R radicals, one of which contains at least 6 carbon atoms, or else which have at least 2 R radicals, each of which has at least 3 carbon atoms. Examples of silanes (SI) which are more preferably alkoxylated using the process according to the invention are cyclohexylmethyldichlorosilane, cyclohexylethyldichlorosilane, phenylmethyldichlorosilane, phenylethyldichlorosilane, dicyclopentyldichlorosilane, dicyclopropyldichlorosilane, n-decyltrichlorosilane, n-undecyltrichlorosilane, n-dodecyltrichlorosilane, n-tridecyltrichlorosilane, n-tetradecyltrichlorosilane, n-pentadecyltrichlorosilane, n-hexadecyltrichlorosilane, and alkyltrichlorosilanes having even longer alkyl chains.

Further examples are silanes (SI) of the general formula (1) having Si—C-bonded polyether chains, e.g. polyethylene glycol or polypropylene glycol chains having 2-20 polyether units. Preferably, these polyether chains are bonded to the silyl group via a propyl spacer. In this context, the process according to the invention is also suitable for mixtures of polyether-functional silanes in which the individual silanes have polyether chains with different chain length. Particular preference is given to silanes (SI) of the general formula (1), which have an Si-bonded methyl group and a polyether chain which has 2-10 ether units and is bonded via a propyl spacer.

The alcohols used in the process according to the invention may in principle be all compounds having an alcoholic hydroxyl group, the boiling point of which is below that of the silane to be alkoxylated. Preferred alcohols have 1 to 6 carbon atoms. Examples are 2-methoxyethanol, n-propanol, i-propanol, n-butanol, i-butanol or n-hexanol. Particular preference is given to using methanol and ethanol and to preparing the corresponding methoxy- or ethoxysilanes. Thus the products contain alkoxy groups $OR^1$ where $OR^1$ is a $C_{1-6}$ alkoxy group, preferably a methoxy or ethoxy group.

Alternatively, it is also possible to use mixtures of various alcohols, for example ethanol-methanol mixtures, in order to arrive at silanes having mixed alkoxy groups. However, preference is given to using pure alcohols.

In the examples which follow, unless stated otherwise in each case, all amount and percentage figures are based on weight, all pressures are 0.10 MPa (abs.) and all temperatures are 20° C.

EXAMPLES

In the present example, hexadecyltrichlorosilane is reacted with methanol in a laboratory double column to give hexadecyltrimethoxysilane. The silane hexadecyltrichlorosilane is metered into the top of the first column at a throughput of 100 kg/h and reacted in countercurrent with ascending methanol vapors to give hexadecyltrimethoxysilane. For this purpose 26 kg/h of methanol are metered into the bottom of the first column. The latter consists of 7 sections filled with random packings. The partly alkoxylated silane is conducted from the bottom of the first column through an intermediate vaporizer into the top of the second column. The second column has a section with 4 bubble-cap trays in the upper region of column 2, which can be bypassed for comparative purposes. 10 kg/h of methanol are metered into the bottom of the second column, in order to complete the alkoxylation. The distillate of the second column is collected and introduced together with the silane into the top of the first column. The product is obtained in the bottom of the second column. The temperature in the bottom of column 1 is 90° C., while it is 140° C. in the bottom of column 2. This temperature profile is run both in example A and in example B.

The table below shows the comparison of the variants without (example A) and with bubble-cap trays (example B), and the metering flow rates. Under otherwise identical boundary conditions, the residual chlorine content can be lowered from 600 ppm to 200 ppm by the use of a single section comprising bubble-cap trays.

|  | Silane in tops of column I | Methanol in bottoms of column I | Methanol in bottoms of column II | Residual HCl in Product |
|---|---|---|---|---|
| Example A* | 100 | 26 | 10 | 600 |
| Example B | 100 | 26 | 10 | 200 |

*not inventive

The invention claimed is:

1. A process for continuously preparing compounds containing SiOC groups, comprising: reacting a silane having silicon-bonded chlorine atoms with an alcohol and optionally also with water to release gaseous hydrogen chloride, at least part of the reaction being performed in a reaction column in which a gaseous phase contains a total of at least 80% by weight of alcohol, hydrogen chloride, any water, and any inert gas, and a liquid phase contains a total of at least 80% by weight of silane, silicon-containing intermediates, compounds containing SiOC groups, and any inert solvent,
   wherein the alcohol is passed repeatedly through the liquid phase
   a) wherein at least one reaction column is provided with internals which pass the gas phase through the liquid phase in bubble form, and/or
   b) wherein at least one reaction column is provided with a vaporizer which operates by a crossflow principle
   wherein the alcohol contains less than 8% water.

2. The process of claim 1, wherein gaseous hydrogen chloride formed is drawn off from the process proximate the top of the reaction column.

3. The process of claim 1, wherein the reaction column internals comprise bubble-cap trays.

4. The process of claim 2, wherein the reaction column internals comprise bubble-cap trays.

5. The process of claim 3, in which the reaction column internals comprise at least 2 bubble-cap trays.

6. The process of claim 1, wherein a vaporizer comprising at least two segments through which a liquid phase from the reaction column flows successively is present, with metered addition and vaporization of alcohol in each segment, and a gaseous alcohol stream which forms in the individual segments is combined and at least partly transferred into the reaction column.

7. The process of claim 1, wherein a vaporizer comprising at least two segments through which a liquid phase from the reaction column flows successively is present, with metered addition and vaporization of alcohol in each segment, and a gaseous alcohol stream which forms in the individual segments is combined and at least partly transferred into the reaction column.

8. The process of claim 6, wherein the vaporizer comprises a poolboiler or kettle, a shell space of which is divided by upright baffle plates into at least 3 individual segments, and a liquid phase from the reaction column flows through these segments by weir overflow at the baffle plates, with addition and vaporization of alcohol in each of these segments, and a gaseous alcohol stream which forms in the individual segments is combined and at least partly transferred into the reaction column.

9. The process of claim 1, in which silanes of the formula (I) are used $$R_nSiCl_{4-n} \quad (1)$$

where
n is 0, 1, 2 or 3, and
R is hydrogen or a monovalent substituted or unsubstituted organic radical.

10. The process of claim 9, wherein at least one silane is selected from the group consisting of silanes having an R radical with at least 10 carbon atoms, silanes having at least 2 R radicals, at least one of which contains at least 6 carbon atoms, and silanes having at least 2 R radicals, each of which has at least 3 carbon atoms.

11. The process of claim 1, in which at least one alcohol has 1 to 6 carbon atoms.

12. The process of claim 1, wherein the compounds containing SiOC bonds are monomeric alkoxysilanes.

13. The process of claim 9, wherein the compounds containing SiOC bonds are monomeric alkoxysilanes.

14. The process of claim 9, wherein the compounds containing SiOC bonds are alkoxysilanes of the formula $$R_nSi(OR^1)_{4-n}$$

where $OR^1$ is a $C_{1-6}$ alkoxy group.

15. The process of claim 9, wherein the alcohol is selected from the group consisting of methanol, ethanol, and mixtures thereof, and the compounds containing SiOC bonds are alkoxysilanes of the formula $$R_nSi(OR^1)_{4-n}$$

where $OR^1$ is a methoxy or ethoxy group.

16. The process of claim 1, wherein the alcohol contains less than 4% water.

17. The process of claim 1, wherein the alcohol contains less than 2% water.

18. The process of claim 1, wherein the component containing SiOC bonds is an alkoxy-functional organopolysiloxane oligomer.

* * * * *